United States Patent [19]
Delk et al.

[11] Patent Number: 5,807,313
[45] Date of Patent: Sep. 15, 1998

[54] BATTERY POWERED SURGICAL IRRIGATOR

[75] Inventors: Michael Delk, North Kingstown; Marco Wo, Providence; Aidan Petrie, Providence; John Mathews, Providence, all of R.I.

[73] Assignee: C. R. Bard, Inc., Murray Hill, N.J.

[21] Appl. No.: 684,397

[22] Filed: Jul. 19, 1996

[51] Int. Cl.[6] .................................................. A61M 1/00
[52] U.S. Cl. ............................................ 604/35; 604/151
[58] Field of Search .............................. 604/151, 35, 32, 604/33, 39, 27, 30

[56] References Cited

U.S. PATENT DOCUMENTS

| | | |
|---|---|---|
| 1,250,928 | 12/1917 | Mechling .............................. 604/131 X |
| 2,416,391 | 2/1947 | Hixson . |
| 2,712,822 | 7/1955 | Gewecke . |
| 2,863,451 | 12/1958 | Barr, Sr. et al. . |
| 3,794,031 | 2/1974 | Bloom . |
| 3,861,383 | 1/1975 | Kovach . |
| 3,966,363 | 6/1976 | Rowley et al. . |
| 4,493,694 | 1/1985 | Wuchinich . |
| 4,525,156 | 6/1985 | Benusa et al. . |
| 4,662,829 | 5/1987 | Nehring . |
| 4,911,609 | 3/1990 | Anderson et al. . |
| 4,935,005 | 6/1990 | Haines . |
| 4,941,872 | 7/1990 | Felix ...................................... 604/39 X |
| 4,946,439 | 8/1990 | Eggers . |
| 4,982,739 | 1/1991 | Hemstreet et al. . |
| 5,019,038 | 5/1991 | Linden . |
| 5,030,202 | 7/1991 | Harris ...................................... 604/39 X |
| 5,120,305 | 6/1992 | Boehringer et al. . |
| 5,142,723 | 9/1992 | Lustig et al. . |
| 5,176,629 | 1/1993 | Kullas et al. . |
| 5,186,714 | 2/1993 | Boudreault et al. . |
| 5,188,591 | 2/1993 | Dorsey, III . |
| 5,195,959 | 3/1993 | Smith . |
| 5,197,460 | 3/1993 | Ito et al. . |
| 5,203,769 | 4/1993 | Clement et al. . |
| 5,224,929 | 7/1993 | Remiszewski . |
| 5,303,735 | 4/1994 | Cerola et al. . |
| 5,322,503 | 6/1994 | Desai . |
| 5,322,506 | 6/1994 | Kullas . |
| 5,368,569 | 11/1994 | Sanese . |
| 5,388,612 | 2/1995 | Cerola et al. . |
| 5,391,145 | 2/1995 | Dorsey, III . |
| 5,429,596 | 7/1995 | Arias et al. . |
| 5,464,391 | 11/1995 | DeVale . |
| 5,484,402 | 1/1996 | Saravia et al. ............................ 604/35 |

*Primary Examiner*—Max Hindenburg
*Attorney, Agent, or Firm*—Arthur Z. Bookstein; Steven G. Saunders

[57] ABSTRACT

A system for irrigating a surgical site is disclosed having a light weight battery powered pumping unit that is directly connectible to an irrigation source, and a handpiece that either irrigates the site with irrigation fluid from the pumping unit or aspirates spent irrigation liquid and biological debris from the site. The handpiece communicates with the site through an elongate wand that passes through an incision to the irrigation site. A spike extending upwardly from a pump head portion of the pumping unit detachably connects the pumping unit to the irrigation source.

27 Claims, 9 Drawing Sheets

BATTERY POWERED SURGICAL IRRIGATOR

FIELD OF THE INVENTION

This invention relates generally to medical irrigation systems and, more particularly, to medical irrigation systems for use in laparoscopic and endoscopic procedures.

BACKGROUND OF THE INVENTION

Laparoscopic suction irrigators are used to deliver irrigation liquid to an internal organ by means of a wand inserted through a cannula placed through an incision in a patient's abdomen. The wand is connected, by tubing, to an irrigation liquid pump and reservoir. The pump may be pneumatically or electrically powered by an external energizing source such as, for example, a source of compressed air. Each mode of power has its advantages and disadvantages. Users who prefer to avoid or are unable to access a pneumatic source may prefer an electrically powered device in which the power source can comprise self-contained batteries. One such device is described, for example, in U.S. Pat. No. 5,484,402 (Saravia et al.). The Saravia device includes a pumping unit with an integral spike insertable into the outlet of a reservoir bag. The pumping unit includes a housing that contains an internal pump, motor and batteries to power the motor. Outlet tubing is connected to the housing to direct irrigation liquid to a handpiece. The handpiece also may be connected by a separate tube to a source of suction to enable spent irrigation liquid and biological debris to be aspirated.

Among the difficulties with the device disclosed in the Saravia patent are that it employs a relatively heavy pump driving system, including eight AA batteries as well as a number of complex internal components to secure the batteries and motor within the device. A commercial embodiment of the device disclosed by this patent, for example, sold under the trade name StrykeFlow™ by Stryker Corporation of Kalamazoo, Mich., weighs approximately 0.874 lbs. Additionally, the irrigation tubing from the pump unit to the handpiece is attached to the pumping unit at its upper end in a manner that causes the pump unit to hang from the reservoir bag at a substantial angle to the vertical. The relatively heavy weight of the device (e.g., about 0.874 lbs.) and the angle at which it causes the device to hang from the saline bag may increase the risk of the device inadvertently becoming detached from the saline bag. In order to reduce that risk, the Saravia device includes an annular rib above the spike, apparently to enhance the frictional connection between the spike and the bag.

It is a desirable practice to remove the batteries from the housing after the device has been used in order to facilitate their proper disposition. It would be desirable, therefore, to provide a device in which the batteries are easily accessible after the device has been used. It also would be desirable to provide a device in which the risk of separation of the self-contained pumping unit from the irrigation bag is reduced. It is among the general objects of the invention to provide such device.

SUMMARY OF THE INVENTION

In one aspect of the invention, a battery powered laparoscopic and endoscopic suction irrigator is configured so that the pumping unit is easy to assemble and dissemble, thereby facilitating both battery removal and assembly of the pumping unit. To that end, the pumping unit includes an upper portion that connects directly to an irrigation reservoir (e.g., saline), and a lower portion that contains the batteries. The upper portion includes a pump, a motor, a motor bracket that surrounds the exterior of the motor and fastens directly to the upper portion, and a pair of flexible clips extending downwardly to detachably couple with a pair of corresponding clip holes in the side walls of the lower portion. During manufacture, after the batteries are inserted into the lower portion, the upper portion is detachably connected to the lower portion by coupling the clips with the clip holes. After use, the batteries may easily be removed from the pumping unit by uncoupling the clips from the clip holes.

In another aspect of the invention, the pumping unit is configured to hang substantially vertically from the irrigation source. To that end, the pumping unit includes an irrigation liquid outlet in the upper portion of the unit, a fluid directing conduit fastened to the irrigation liquid outlet port, an irrigation tubing connected to the fluid directing conduit to direct irrigation fluid downwardly, and a wire extending through the bottom of the pumping unit to connect with the motor and batteries.

In yet another aspect of the invention, the pumping unit is lighter and uses less power than the prior art device. To that end, a pump and small six volt motor that requires only four 1.5 volt AA batteries are employed. The reduced overall weight of the pumping unit enables the outer surface of the spike to be smoothly tapered and thus does not require ribs to frictionally and securely couple with the irrigation source.

It is among the objects of the invention to provide a light weight laparoscopic and endoscopic battery powered irrigator that is easier to assemble and disassemble.

It is another object of the invention to provide a laparoscopic and endoscopic irrigator that facilitates battery removal.

It is yet another object of the invention to provide a light weight, battery powered irrigation apparatus for laparoscopic and endoscopic procedures that connects directly to and hangs substantially vertically from an irrigation bag.

BRIEF DESCRIPTION OF THE DRAWINGS

The foregoing and other objects and advantages of the invention will be appreciated more fully from the following further description thereof with reference to the accompanying drawings wherein.

DESCRIPTION OF THE ILLUSTRATIVE EMBODIMENT

Figure 1:
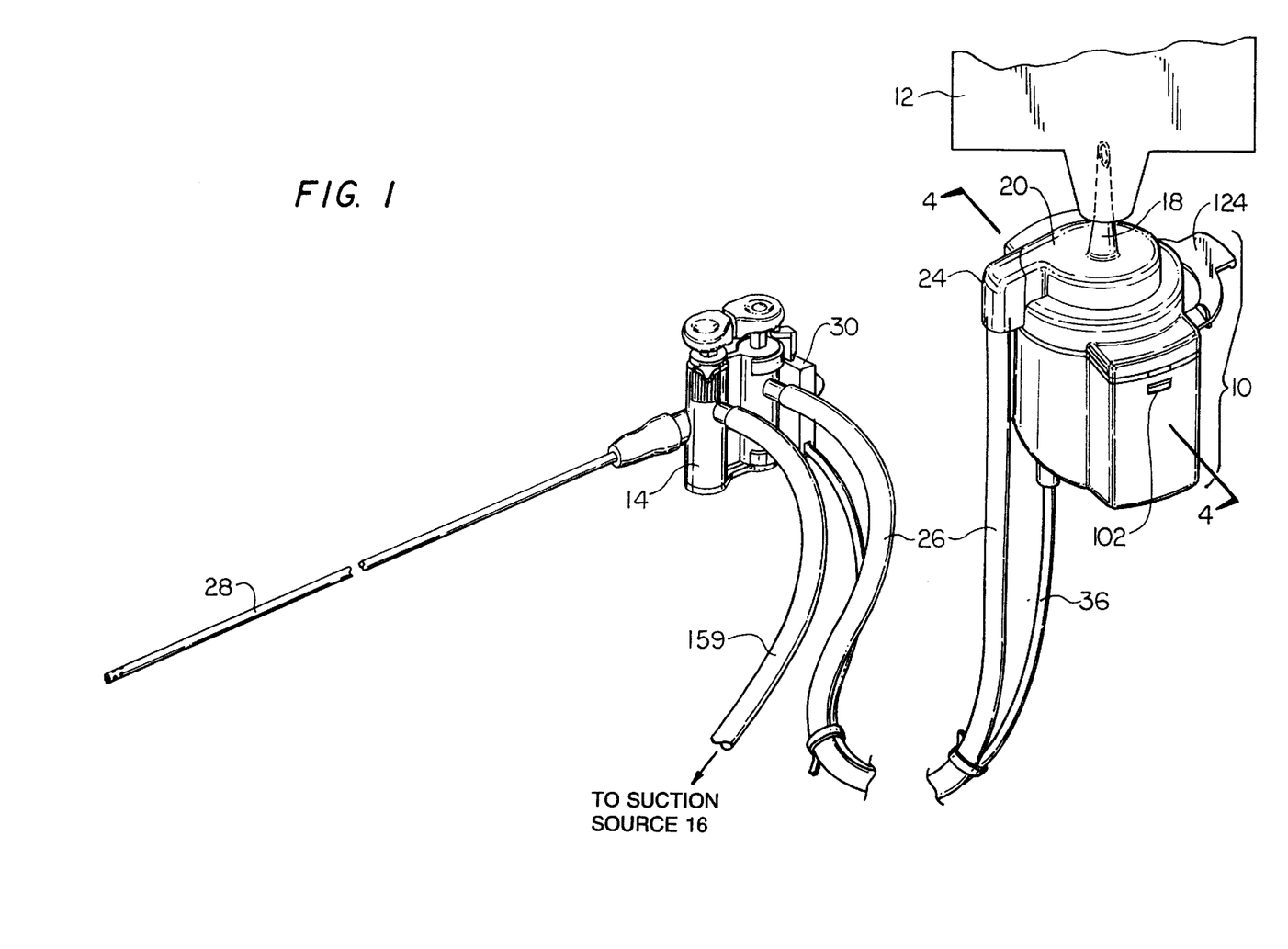
FIG. 1 is a perspective view of the irrigation system in accordance with the invention.

FIG. 1 shows the main components of the suction irrigation system of the present invention, which includes a battery powered pumping unit 10 that is detachably secured to an irrigation source 12 (e.g., a saline bag), and a suction and irrigation handpiece 14 that is connected to both the pumping unit 10 and an external suction source 16. The pumping unit 10 receives irrigation liquid from and is detachably secured to the irrigation source 12 by means of a spike 18 extending upwardly from a pump head 20 in the pumping unit 10. The pump head 20 forms an outlet orifice 22 (FIG. 3) to which a fitting 24 is attached that forms defines a path 25 (shown in phantom in FIG. 3) for directing irrigation liquid downwardly. A flexible irrigation tubing 26 connected to the fitting 24 extends downwardly along the exterior of the pumping unit 10 to the handpiece 14. The handpiece 14 directs irrigation liquid to an irrigation site within a patient's body through an elongate wand 28 that may be advanced to the irrigation site through a laparoscopic cannula. An electric switch 30 connected to the handpiece 14 energizes the pumping unit 10 by means of first and second switch wires 32 and 34 (FIG. 4) extending between the switch 30 and the pumping unit 10 within a flexible insulated conduit 36.

Figure 2:
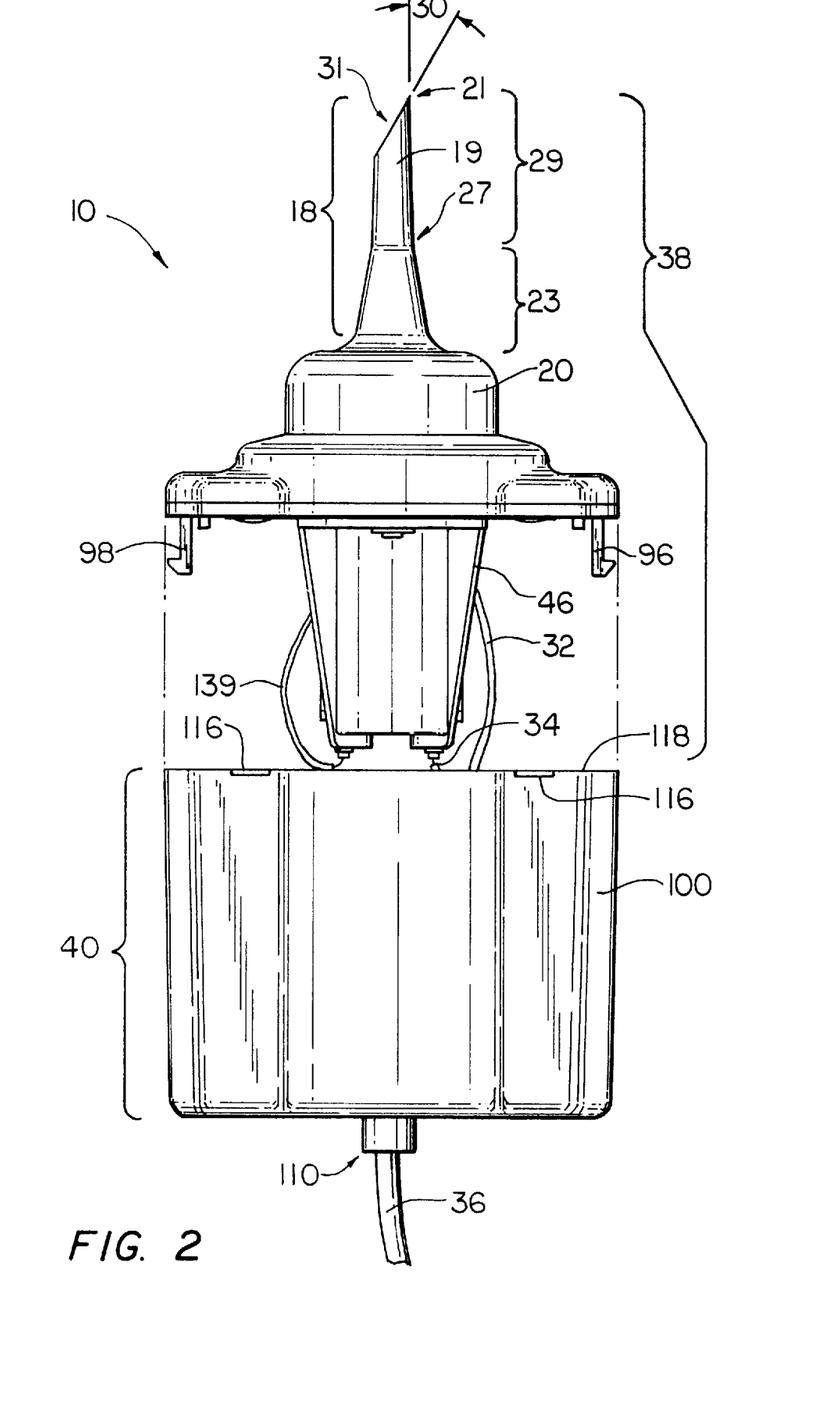
FIG. 2 is a front partially exploded view of the pumping unit in which the upper portion is separated from the lower portion.

FIG. 2 is a partially exploded view of the pumping unit 10, which may be considered as having an upper portion 38 that is detachably connected to a lower portion 40. The upper portion 38 contains a centrifugal pump that receives and pumps irrigation liquid to the handpiece 14, and the lower portion 40 contains batteries 41 that energize the pump in the upper portion 38. As shown in more detail in FIGS. 3–6, the upper portion 38 includes the pump head 20 to receive irrigation liquid through the spike 18, a planar motor deck 42 connected to the pump head 20, a single speed six volt D.C. motor 44 connected to the lower side of the motor deck 42 by a motor bracket 46, and first, second, and third battery contacts 47, 48, and 50 connected to the lower side of the motor deck 42. As discussed in more detail below, the battery contacts 47, 48, and 50 are positioned to contact the batteries 41 within the lower portion 40 of the pumping unit 10. A motor shaft 52, extending from the top of the motor 44, through a hole 54 in the motor deck 42 and into the pump head 20, is connected to a centrifugal impeller 56 within the pump head 20. When energized, the motor 44 rotates the motor shaft 52, which responsively rotates the centrifugal impeller 56 within the pump head 20.

As noted above, the spike 18 removably secures the pumping unit 10 to an outlet of the irrigation source 12 by means of a friction engagement between the smooth outer surface of the spike 18 and a diaphragm (not shown) at the outlet of the irrigation source 12. To that end, as shown in FIG. 2, the spike 18 may include a hollow tapered cylinder 19 extending upwardly from (and integral with) the pump head 20 and terminating at a liquid inlet orifice 31 at an upper end of the cylinder 19. The upper end of the cylinder 19 may have a point 21, formed by a thirty degree angle cut across the upper end of the cylinder 19, to penetrate through the diaphragm in the irrigation source 12. The taper in the cylinder, which more securely frictionally retains the spike 18 to the irrigation source 12 than a non-tapered cylinder 19, narrows the diameter of the cylinder 19 as it extends upwardly from the pump head 20. Accordingly, the cylinder 19 has a first tapered portion 23 extending from the base of the cylinder 19 to a transition point 27 on the cylinder 19, and a narrower, second tapered portion 29 extending from the transition point 27 to the upper end of the cylinder 19. The taper angle of the first tapered portion 23 is selected to resist, but not prevent, the insertion of the first tapered portion 23 through the diaphragm. Although it is preferable that the first tapered portion 23 not be inserted through the diaphragm, the first tapered portion 23 nevertheless will support the entire weight of the pumping unit 10. The taper angle of the second tapered portion 29 is selected to enable the second tapered portion 29 to be inserted through the diaphragm, and to support the entire weight of the pumping unit 10. Respective taper angles of ten degrees and two degrees (relative to the longitudinal axis of the cylinder) for the first and second tapered portions 23 and 29 have yielded satisfactory results. In addition, the outer surface of the cylinder 19, manufactured from a relatively hard plastic, may be smooth and should securely support the entire weight of the pumping unit 10 without any ridges or other rough surfaces that could increase the effect of the friction fit between the spike 18 and the diaphragm.

Figure 4:
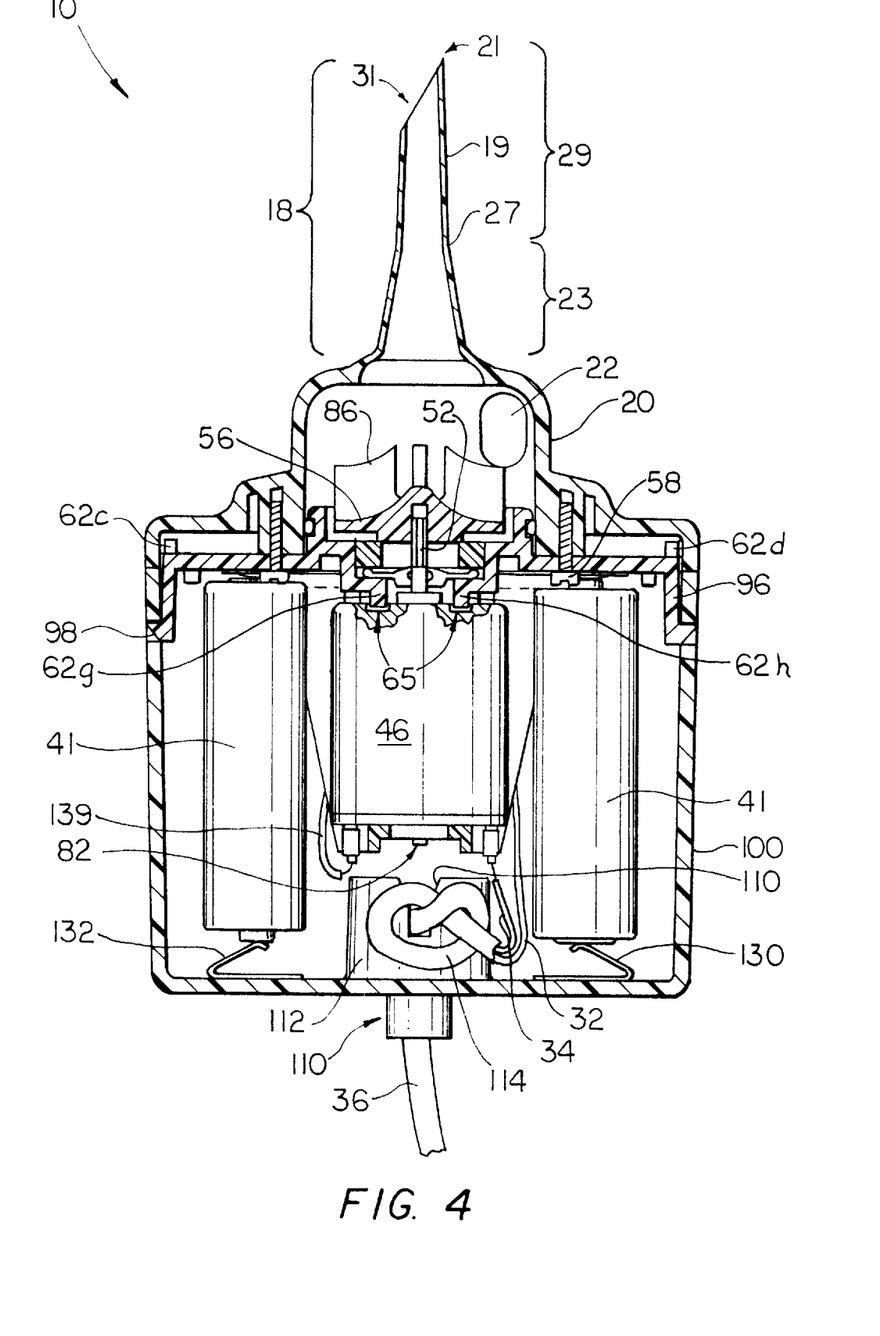
FIG. 4 is a cross-sectional view of the pumping unit as seen along line 4—4 of FIG. 1.
Figure 5:
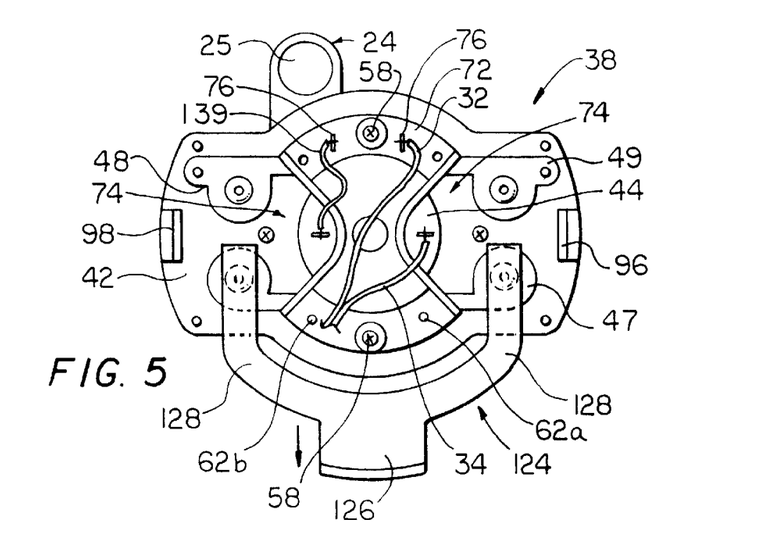
FIG. 5 is a bottom view of the upper portion of the pumping unit.
Figure 6:
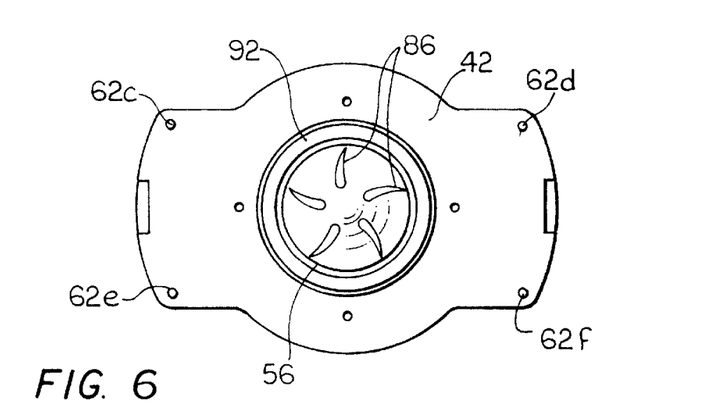
FIG. 6 is a plan view of the deck and impeller with the pump head removed.

A plurality of location bosses, referred to generally as reference numeral 62, extend from both the top and bottom surfaces of the deck 42, simplifying the manufacturing process and strengthening the connection between the various elements in the pumping unit 10. FIG. 5 shows, for example, bosses 62a and 62b as being aligned with holes in the first battery contact 47 (shown in FIG. 5 with the bosses 62a and 62b through them) to precisely position the first battery contact 47 on the deck 42. In addition to facilitating assembly, the bosses 62a and 62b prevent the battery contact 47 from sliding relative to the deck 42, thus strengthening the connection between the contact 47 and the deck 42. As a second example, the four bosses 62c, 62d, 62e, and 63f on the top of the deck 42 (FIGS. 4 and 6) are positioned so that when the deck 42 is connected to the pump head 20, each boss is substantially exactly adjacent to the inner surface of the lower end of the pump head 20. Accordingly, when the motor deck 42 is fastened to the pump head 20 during assembly, the four bosses 62c–62f snap into the lower end of the pump head 20, thereby securely connecting the motor deck 42 to the pump head 20. As a further example, bosses 62g and 62h also may be included on the lower surface of the deck 42 to cooperate with corresponding boss dimples 65 (shown in phantom in FIG. 4) formed on the top surface of the motor 44. This prevents the motor 44 from rotating relative to the pumping unit 10 during operation.

As noted above, the motor bracket 46 secures the motor 44 to the upper portion 38 of the pumping unit 10 to prevent the motor 44 from detaching from the upper portion 38 of the pumping unit 10 when disassembled. FIGS. 2–5 show the motor bracket 46, which may be made from a hard plastic. The motor bracket 46 preferably includes a bottom wall 66, a cylindrical body 68 extending upwardly from the bottom wall 66 to a rim 70, and a securing flange 72 extending radially outwardly from the rim 70. The cylindrical body 68, which has an inner diameter that approximates the diameter of the motor 44, forms a cylinder that surrounds the exterior of the motor 44. The cylindrical body 68 has two open sides that expose the positive and negative terminals 73a and 73b on the bottom of the motor 44. A plurality of holes are formed by the flange 72 to receive screws 58 that secure the bracket 46 to the deck 42, and for coupling with several of the locator bosses 62. Two contact holes 76 may also be formed in the rim 70 to enable the ends of the second battery contact 48 and the third battery contact 50 to be exposed through the rim 70 for connection with the switch wires 32 and 34. A hole 80 may be formed in the bottom wall 66 to receive a boss 82 (FIG. 5) extending from the bottom of the motor 44.

The centrifugal impeller 56, preferably made from a hard plastic material, may have a circular body 84 with five vanes 86 equally spaced about the center of the top surface of the body 84. The outlet orifice 22 is positioned in the side of the pump head 20 so that the centrifugally accelerated irrigation liquid will be emitted through the outlet orifice 22 at a relatively high flow rate. After passing through the outlet orifice 22, the irrigation liquid will immediately be directed downwardly by the fitting 24 and the flexible irrigation tubing 26 to the handpiece 14.

The motor 44 and batteries 41 should not be exposed to irrigation liquid because such exposure can short circuit the pumping unit 10. To that end, the motor 44 and lower portion 40 of the pumping unit 10 are fluidly sealed from the interior of the pump head 20 by the combination of a sealing gasket 88 disposed in a circular recess 90 in the upper surface of the motor deck 42, and an O-ring 92 that circumscribes the circular recess 90. The gasket 88 and O-ring 92 may be made from any sealing material such as, for example, flexible rubber. The gasket 88 may be retained in the recess 90 by an annular securing ring 94 having a plurality of grooves (not shown) that frictionally secure the ring 94 to the interior wall of the recess.

Two flexible deck clips 96 and 98 extend downwardly from each side of the deck 42 to detachably connect the upper portion 38 of the pumping unit 10 to the lower portion 40 of the pumping unit 10. The clips 96 and 98 each have a planar body and a lower tooth that couples with the lower portion 40 of the pumping unit 10.

The lower portion 40 of the pumping unit 10 includes a battery cup 100 having side walls that define two oppositely positioned rectangular holes 102 and 104 (FIG. 3), and four AA 1.5 volt batteries 41 contained in the battery cup 100. The rectangular holes 102 and 104 are aligned respectively with the clips 96 and 98 to removably couple the upper portion 38 of the pumping unit 10 to the lower portion 40 of the pumping unit 10. The interior of the battery cup 100 may be molded to have four battery supporting projections 108 that support the batteries 41 in a vertical orientation. This battery orientation aligns each of the four batteries 41 with their respective battery contacts 47, 48, and 50.

A wire hole 110 formed in the bottom of the battery cup 100 enables the switch wires 32 and 34 to pass through the bottom of the battery cup 100 to the motor 44 and battery contacts 47, 48, and 50. The arrangement of the switch wires 32 and 34 do not cause the pumping unit 10 to hang non-vertically from the irrigation source 12. The wires are secured in the battery cup 100 by a semi-cylindrical wire securing wall 112 that extends upwardly from the bottom interior wall of the battery cup 100. The switch wires 32 and 34 may be tied in a small knot 114 and inserted through a notch 116 formed in the cylindrical wall 112 so that the knot 114 is on the side of the cylindrical wall 112 that is opposite the wire hole 110.

The battery cup 100 has an upper rim 118 defining two depressions 120 and 122 for slidably receiving an insulator 124 that breaks the electrical contact between at least one battery 41 and the corresponding battery contact 47, 48, or 50 on the deck 42. The insulator 124, which may be a U-shaped member, ensures that the motor 44 will not accidentally be energized prior to use. As shown in more detail in FIG. 5, the U-shaped member may have a handle 126 for gripping the member, and two arms 128 that slide into the battery cup 100 to insulate the at least one of the battery contacts 47, 48, 50 from any corresponding battery 106.

A first conductive leaf spring contact 130 may be disposed between two of the projections 108 and a second conductive leaf spring contact 132 may be disposed between the other two projections 108 to normally force the batteries 41 upwardly to contact the battery contacts 47, 48, and 50. As discussed in greater detail below, the first spring contact 130 serially connects two of the four batteries 41 (the first battery pair 134) and the second leaf spring contact 132 serially connects the remaining two batteries 41 (the second battery pair 136).

Figure 7:
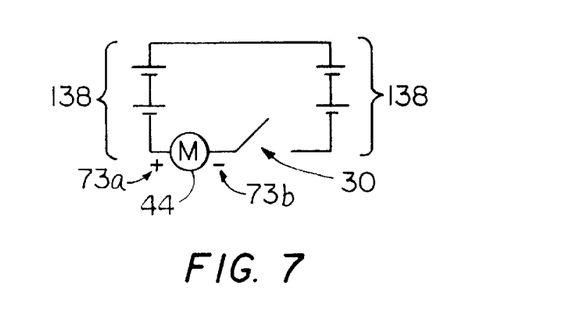
FIG. 7 is a schematic illustration of the electrical configuration of the batteries, motor, and switch.

FIG. 7 schematically illustrates the electrical configuration of the batteries 41, switch 30, and motor 44. More particularly, the four batteries 41 are serially connected to effectively form a six volt battery 138 that is serially connected between the positive terminal 73a of the motor 44 and the switch 30. The switch 30 is connected between the positive end of the effective battery 138 and the negative terminal 73b of the motor 44. The motor 44 therefore is energized when the switch 30 is closed.

Figure 3:
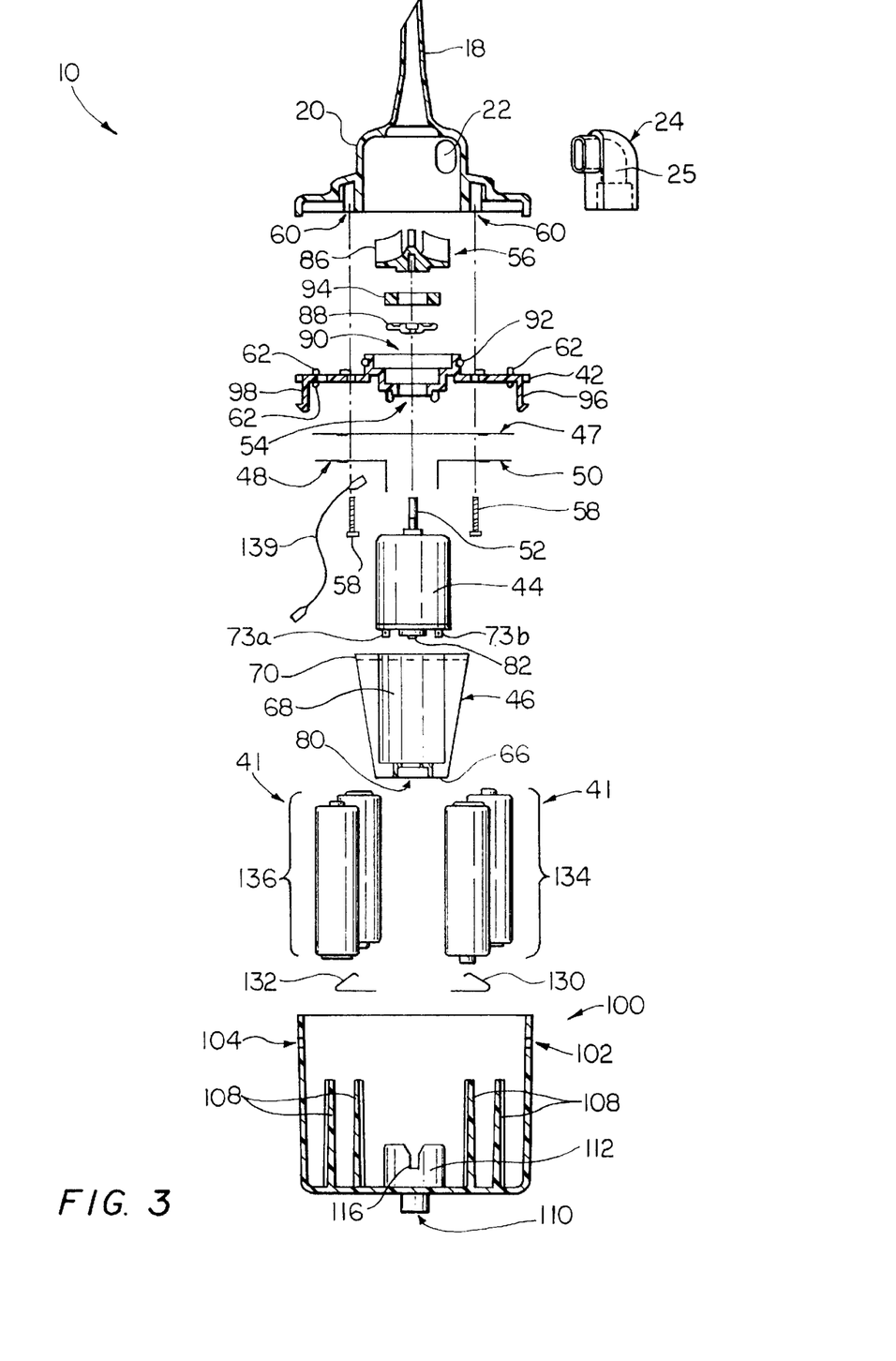
FIG. 3 is an exploded view of the pumping unit showing its internal components.

FIGS. 3 and 5 show the position of the batteries 41, switch wires 32 and 34, and motor 44 in the assembled pumping unit 10, in which the first battery contact 47 serially connects the first battery pair 134 to the second battery pair 136 to form the effective battery 138 having a positive end and a negative end. The negative end of the effective battery 138 contacts the second battery contact 48 on the deck 42 which itself is serially connected to the positive terminal 73a of the motor 44 by means of an electrically conductive jumper wire 139. The positive end of the effective battery 138 contacts the third battery contact 50, which is attached the first switch wire 32, and the second switch wire 34 is attached to the negative terminal 73b of the motor 44. As discussed in more detail below, the switch 30 is mounted to the handpiece 14 and electrically connects the first and second wires 32 and 34, thus completing the circuit and energizing the motor 44.

The handpiece 14 may be any conventional laparoscopic or endoscopic handpiece, such as that disclosed in U.S. Pat. No. 5,388,612 (Cerola et al.), the entire disclosure of which is incorporated by reference herein. FIGS. 8–12 show the handpiece 14, which may be a trumpet valve handpiece, having an irrigation inlet port 140, a suction port 142, and an outlet port 150 for either suction or irrigation. The irrigation inlet port 140, suction port 142, and outlet port 144 are each integral with respective irrigation, suction, and outlet cylinders 146, 148, and 150. Both the irrigation and suction cylinders 146 and 148 are in fluid communication with the outlet cylinder 150 by means of irrigation and suction plungers 152 and 154 disposed respectively in the irrigation and suction cylinders 146 and 148. The plungers 146 and 148 each have respective irrigation and suction communication holes 156 and 158 and are spring biased so that the communication holes 156 and 158 are located in a horizontal plane above the highest horizontal plane of the outlet cylinder 150.

When the irrigation plunger 152 is depressed, the location of the irrigation communication hole 156 moves downwardly against the force of the spring to fluidly link the irrigation inlet port 140 and the outlet cylinder 150. This link enables irrigation liquid to communicate with the outlet cylinder 150, consequently causing irrigation liquid to be emitted through the outlet port 144. Similarly, when the suction plunger 154 is depressed, the location of the suction communication hole 158 moves downwardly against the force of the spring to fluidly link the suction port 142 and the outlet cylinder 150. This link enables the suction source 16 to communicate with the outlet cylinder 150, thus creating an aspiration at the outlet port 144.

During use, the irrigation inlet port 140 receives irrigation liquid from the pumping unit 10 through the flexible irrigation tubing 26, and the suction port 142 is connected to the suction source through suction tubing 159. The outlet cylinder 150 may have a fitting 160 at one end to couple with the wand 28, and a removable cap 162 at the other end. The removable cap 162 may be removed and another surgical tool, such as an electrocautery device, may be inserted through both the outlet cylinder 150 and the wand 28 to further treat an internal surgical site. The irrigation plunger 152 may have a raised surface on its top surface to physically distinguish it from the suction plunger 154.

Figure 10:
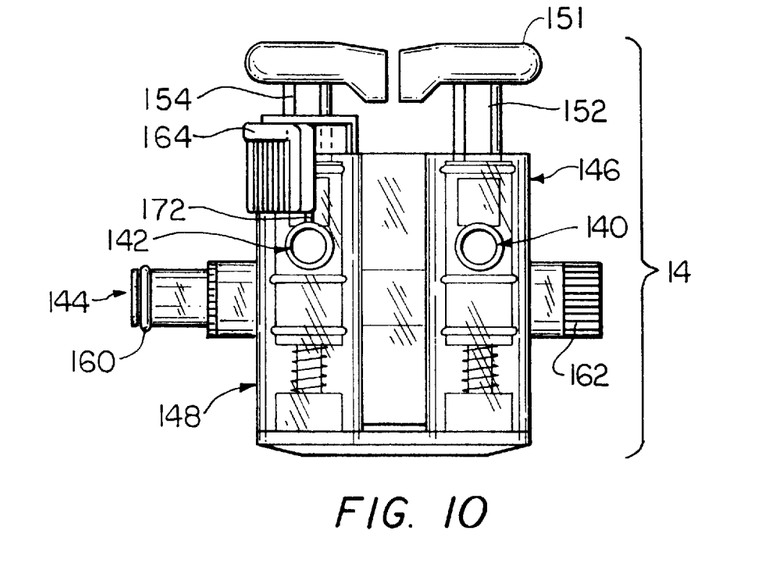
FIG. 10 is a front view of the handpiece in which the suction plunger is not depressed.
Figure 11:
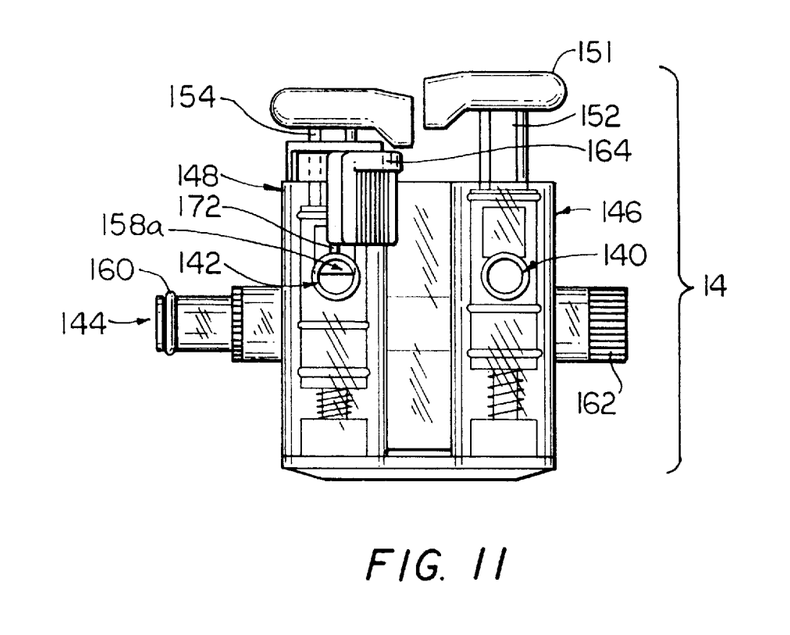
FIG. 11 is a front view of the handpiece in which the suction plunger is partially depressed by the sliding button.
Figure 12:
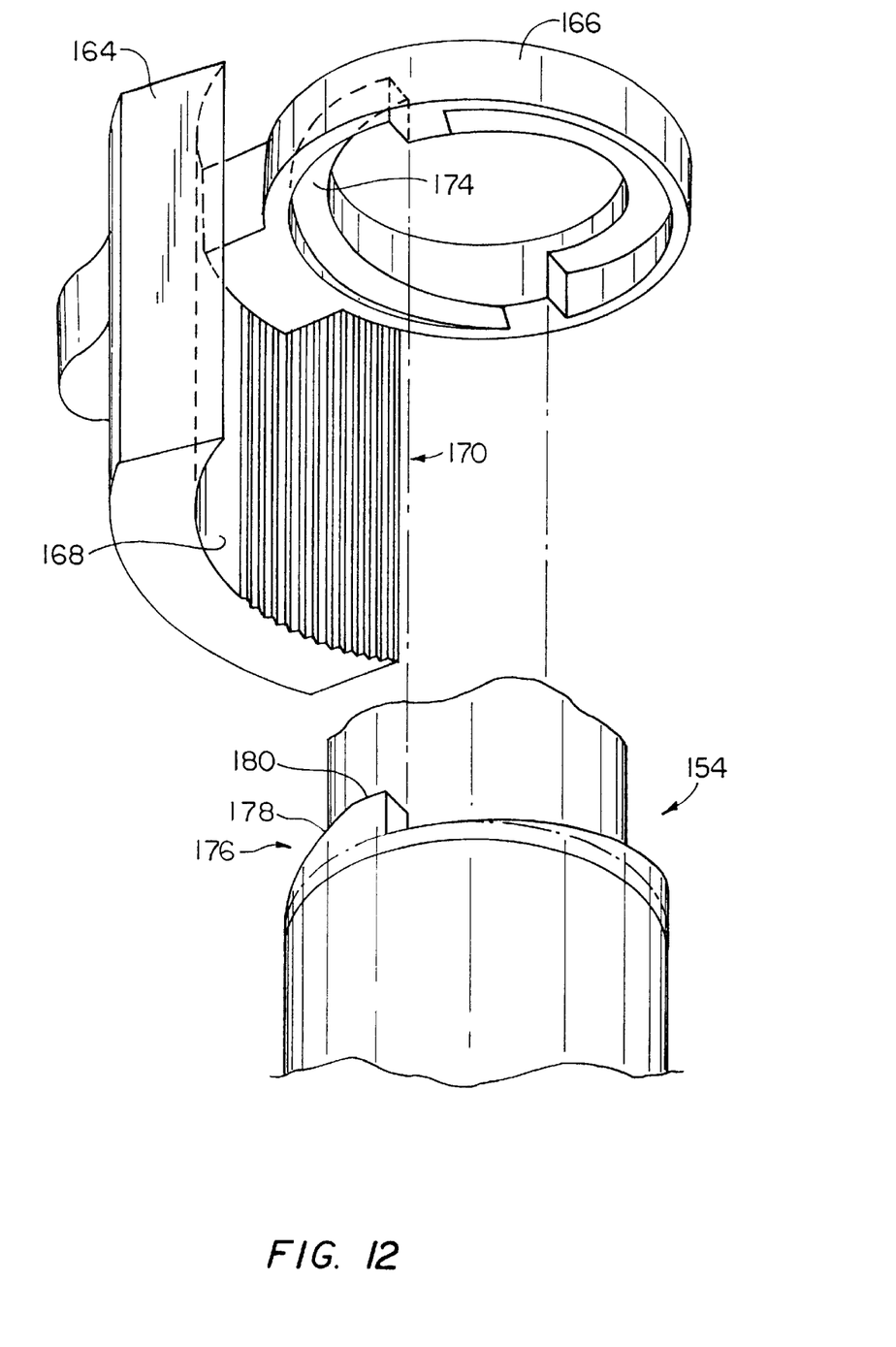
FIG. 12 is an exploded perspective view of the inner surface of the button and collar and their cooperation with the suction plunger.

FIGS. 10–12 illustrate the details of a sliding lock ring 164 that may partially depress the suction plunger 158, creating a small suction that withdraws smoke created within a patient's body by electrocautery procedures. For example, when the ring 164 is positioned at the left side of the suction cylinder 148 (FIG. 10), the suction plunger 158 is not depressed and the suction communication hole 158 does not link the suction port 142 with the outlet cylinder 150. In contrast, when the ring 164 is slid to the right side of the suction cylinder 148 (FIG. 11), the suction plunger 158 is depressed slightly, thus linking only a small part 158a of the suction communication hole 158 with the outlet cylinder 150. This small linked part 158a of the suction communication hole 158 provides the small suction to the outlet cylinder 150.

FIG. 12 shows the details of the ring 164, which includes an annular collar 166 that secures the ring 164 to the suction plunger 158, and an inner surface 168 having a plurality of grooves 170. Each of the grooves 170 may couple with a single ridge 172 (FIGS. 10 and 11) on the suction cylinder 148 to provide a means for locking the button 164 into a predetermined position between the right and left sides of the suction cylinder 148. The collar 166 has a sloped, inner camming surface 174 that depresses the suction plunger 154 by means of a plunger flange 176 extending from the suction plunger 154. The flange 176 has a sloped portion 178 and a horizontal portion 180 that cooperate with the sloped inner camming surface 168 such that when the ring 164 is on the left side of the suction cylinder 148, the sloped portion 178 of the flange 176 is disposed entirely within and corresponds exactly with the camming surface 174. As the ring 164 is slid to the right side of the suction cylinder 148, the inner camming surface 174 slides upwardly along the sloped part 178 of the flange 176 to force the suction plunger 158 downwardly at a rate that corresponds with the slope of the inner camming surface 174. The ring 164 is retained in position at the right side of the suction cylinder 148, thus maintaining the suction plunger 158 in a partially depressed position, by the ridge 172 that couples with one of the grooves 170 on the inner surface 168 of the ring 164.

Figure 8:
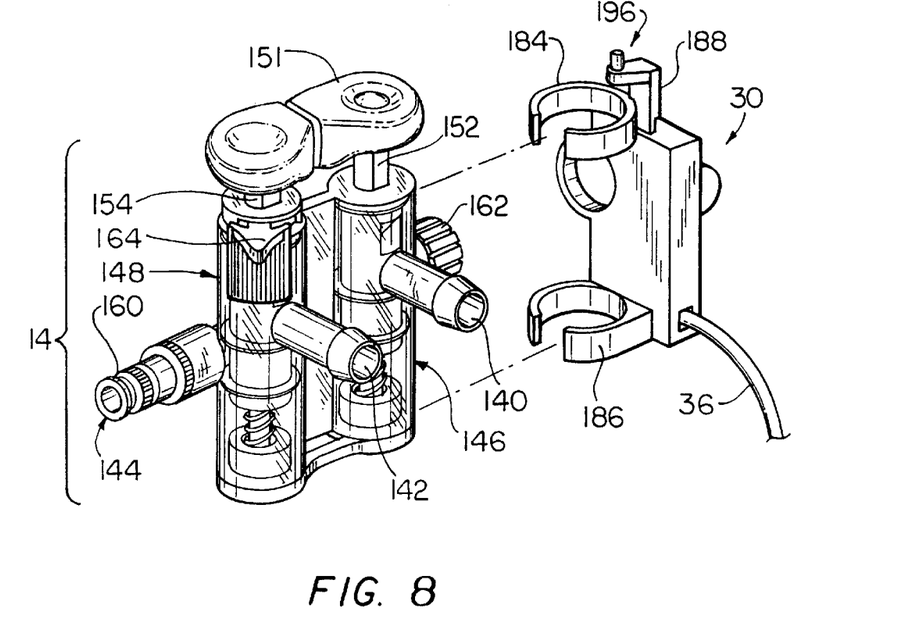
FIG. 8 is a perspective view of the handpiece showing the front and side of the handpiece.
Figure 9:
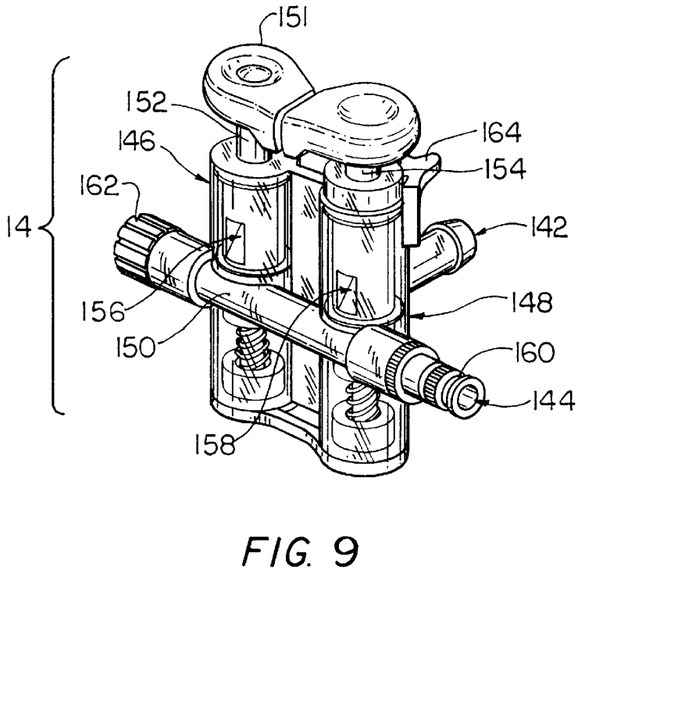
FIG. 9 is a rear perspective view of the handpiece.
Figure 13:
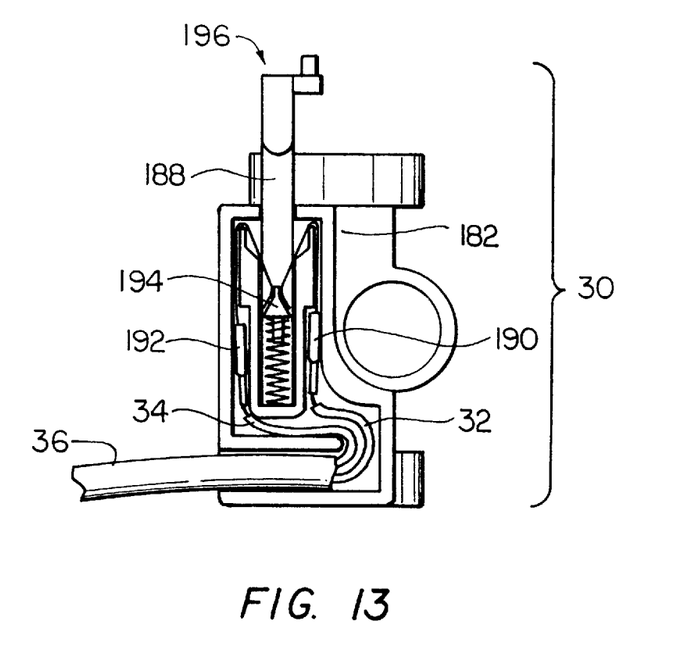
FIG. 13 is a front view of the switch with the front cover removed to show its internal components.

The electric switch 30 may be any suitable switch, or may be the switch 30 shown in FIGS. 8 and 13. Specifically, the switch 30 may include a body 182 having integral top and bottom clips 184 and 186 that are sized to clip about the outside of the irrigation cylinder 146 on the handpiece 14.

As shown in FIG. 12, the switch 30 has a separating plunger 188 that is spring biased upwardly, within the interior of the body 182, to normally separate first and second switch conductors 190 and 192 with a triangular wedge 194 on the outer surface of the separation plunger 188. When the separating plunger 188 is depressed, the first switch conductor 190 flexes against the second switch conductor 192, thus electrically contacting the two switch conductors 190 and 192. Since the first switch conductor 190 is connected to the first switch wire 32 and the second switch conductor 192 is connected to the second switch wire 34, this electrical contact between the switch conductors 190 and 192 completes the circuit between the positive end of the effective six volt battery 138 and the negative terminal 73b of the motor 44. As shown in FIG. 8, the top of the separating plunger 188 has a projection 196 that connects to the underside of a finger knob 151 on the irrigation plunger 152. This enables a user to simultaneously move both the separating plunger 188 and the irrigation plunger 152, thus energizing the motor 44 whenever the irrigation plunger 152 is depressed.

When the suction and irrigation system is in use, the spike 18 is inserted through a membrane in the saline bag 12, the wand 28, suction tubing 159, and irrigation tubing 26 are all connected to the handpiece 14, and the U-shaped insulator 124 is withdrawn from the pumping unit 10. The wand 28 is then inserted through a sheath, extending from a patient's abdomen, to the irrigation site. When the irrigation plunger 152 on the handpiece 14 is depressed, the switch conductors 190 and 192 in the switch 30 contact to electrically connect the motor 44 to the batteries 41. This causes irrigation fluid to serially flow through the fitting 24 and flexible irrigation tubing 26 to the handpiece irrigation inlet port 140. Irrigation fluid then passes through the irrigation plunger communication hole 156, through the outlet cylinder 150, outlet port 144, and wand 28, to the irrigation site. Suction may be applied to the site by depressing the suction plunger 158 on the handpiece 14, which fluidly communicates the suction port 142 with the outlet cylinder 150, drawing spent irrigation liquid and biological debris from the site. If the wand 28 becomes clogged, both the suction plunger 158 and the irrigation plunger 152 may be depressed to create a turbulence within the wand 28 that may dislodge the clogging matter.

It should be apparent from the foregoing that the invention improves over the prior art in a number of ways. Specifically, the improved pumping unit 10 should hang more vertically from the saline bag reservoir 12 than prior art battery powered pumping units. Furthermore, the cooperation between the clips 96 and 98 extending from the motor deck 42 and rectangular holes 102 and 104 in the sides of the battery cup 100 enable the batteries 41 to be removed from the pumping unit 10 with relative ease. In addition, the bosses 62 on the motor deck 42 simplify manufacture and strengthen the connection between the elements of the pumping unit 10. Furthermore, the motor bracket 46 mounts the motor 44 to the pump head 20 so that the battery cup 100 does not have to be specially molded to support the motor 44, in addition to the batteries 41, thus reducing manufacturing costs. Finally, the pumping unit is lighter and uses less power since it only requires a six volt motor and four AA 1.5 volt batteries to deliver irrigation liquid at a satisfactory flow rate. This reduced weight (e.g., about 0.433 lbs. instead of about 0.874 lbs. for the previously discussed irrigator) enables the spike to frictionally secure the pumping unit 10 to the irrigation liquid reservoir by the smooth outer surface of the spike only.

It should be understood that the foregoing description of the invention is intended merely to be illustrative thereof and that other modifications, embodiments, and advantages of the invention may be apparent to those skilled in the art without departing from its spirit.

Having thus described the invention, what we desire to claim and secure by Letters Patent is:

1. A pump system for irrigating a surgical site, the pump system comprising:
    a pumping unit being directly connectible to an irrigation source, the pumping unit comprising:
        a pump head forming a fluid inlet orifice and a fluid outlet orifice, the pump head having a longitudinal axis;
        a motor having a shaft extending into the pump head;
        an impeller connected to the shaft within the pump head;
        a motor deck secured to the pump head;
        a motor bracket connected to the motor deck, the motor bracket having a portion engageable with the bottom wall of the motor to secure the motor to the motor deck;
        a battery; and
        a battery case to contain the battery, the battery case being detachably connected to the motor deck;
        the motor bracket being independent of the battery case whereby the motor deck, the motor and the bracket, as a unit, can be attached to and detached from the battery case;
    a fitting connected to the fluid outlet orifice and being external to the pump unit, the fitting forming a fluid flow path that is substantially parallel to the longitudinal axis;
    a handpiece having an electric switch and a handpiece fluid inlet, the switch electrically connecting the battery to the motor to energize the motor; and
    flexible irrigation tubing extending from the fitting to the handpiece fluid inlet.

2. The pump system as defined by claim 1 wherein a segment of the flexible irrigation tubing extends from the fitting to the bottom of the battery case, the segment being normally substantially parallel to the longitudinal axis of the pump head.

3. The pump system as defined by claim 1 wherein the electric switch includes a wire and the battery case includes a bottom wall that forms a wire hole, the wire extending from the switch through the wire hole.

4. The pump system as defined by claim 1 wherein the pump head includes a spike extending upwardly, the spike defining the fluid inlet orifice.

5. The pump system as defined by claim 1 wherein the motor deck comprises:
    a top surface;
    a bottom surface; and
    a boss extending from at least one of the deck top surface or deck bottom surface.

6. The pump system as defined by claim 5 wherein the boss extends from the deck bottom surface; and
    the motor has a top surface that forms a dimple, the boss mating with the dimple.

7. The pump system as defined by claim 5 wherein a plurality of bosses extend from at least one of the deck top surface or the deck bottom surface.

8. The pump system as defined by claim 5 wherein the motor bracket defines an aperture that mates with the boss, the boss extending from the deck bottom surface.

9. The pump system as defined by claim 8 wherein
    the motor includes a bottom surface and a motor boss extending from the motor bottom surface; and
    the motor bracket has a bottom wall that defines a hole, the motor boss mating with the bracket hole to secure the motor within the motor bracket.

10. The pump system as defined by claim 1 wherein
    the motor deck includes a flexible clip extending downwardly; and
    the battery case includes a side wall that defines an aperture, the clip mating with the aperture to detachably connect the motor deck to the battery case.

11. A pump system for irrigating a surgical site with irrigation liquid from a reservoir, the reservoir having a diaphragm that fluidly seals an orifice formed by the reservoir, the pump system comprising:
    a pumping unit comprising:
        a housing for containing components of the pumping system;
        a pump head having a spike and a fluid outlet orifice, the spike forming a fluid inlet orifice, the spike penetrating through the diaphragm to fluidly communicate the reservoir and the inlet orifice of the pump head;
        a motor; and
        a motor bracket connected to the pump head and having a portion engageable with the bottom wall of the motor for connecting the motor to the pump head, the bracket and pump head comprising the sole means for securely supporting the motor;
        the pump head, motor bracket and motor being detachably connected, as a unit, to the housing;
    a handpiece having a handpiece fluid inlet; and
    an irrigation tubing to fluidly communicate the pump head outlet orifice and the handpiece fluid inlet.

12. The pump system as defined by claim 11 wherein the pump unit further comprises:
    a battery; and
    a battery case to contain the battery;
    the pump head having a clip extending downwardly,
    the battery case having a side wall that defines an aperture, the clip mating with the aperture to detachably connect the pump head to the battery case.

13. The pump system as defined by claim 12 wherein the handpiece includes an electric switch for connecting the battery to the motor.

14. The pump system as defined by claim 11 further comprising a fitting externally connected to the fluid outlet orifice on the pump head, the pump head having a longitudinal axis, the fitting forming a fluid flow path that is substantially parallel to the longitudinal axis.

15. A pump system for irrigating a surgical site comprising:
    a pump unit having a longitudinal axis, the pump unit being adapted to be suspended from a reservoir of irrigation liquid in an orientation in which the axis is substantially vertical, the pump unit comprising:
        a fluid inlet orifice; and
        a fluid outlet orifice;
    a fitting connected to the fluid outlet orifice and being external to the pump unit,
    the fitting forming a fluid flow path that is substantially parallel to the longitudinal axis of the pump unit;
    a handpiece having a handpiece fluid inlet; and
    an irrigation tubing extending from the fitting to the handpiece fluid inlet.

16. The pump system as defined by claim 15 wherein the pump unit further comprises:

a pump head that defines the fluid inlet and fluid outlet;

a motor deck secured to the pump head;

a motor; and a motor bracket connected to the motor deck to secure the motor to the motor deck.

17. The pump system as defined by claim 16 wherein the motor deck has a clip extending downwardly and the pump unit further comprises a battery case having a side wall that defines an aperture, the clip mating with the aperture to detachably connect the motor deck to the battery case.

18. The pump system as defined by claim 16 wherein the motor deck comprises:

a top surface;

a bottom surface; and a boss extending from at least one of the deck top surface or the deck bottom surface.

19. The pump system as defined by claim 15 wherein the pump unit inlet orifice is defined by a spike, the spike penetrating a diaphragm that fluidly seals an orifice formed by an irrigation liquid reservoir.

20. The pump system as defined by claim 16 wherein the motor is a six volt motor.

21. The pump system as defined by claim 15 wherein the pump unit further comprises:

a pump head that forms the fluid inlet orifice and the fluid outlet orifice;

a battery;

a battery casing to contain the battery, the battery casing being detachably connected to the pump head;

a battery contact connected to the pump head; and a battery insulating member slidably disposed between the battery and the battery contact.

22. The pump system as defined by claim 21 wherein the battery includes four 1.5 volt batteries.

23. The pump system as defined by claim 15 further comprises a wand detachably connected to the handpiece.

24. A pump system for irrigating a surgical site comprising:

a pump unit, a handpiece disposed remotely from the pump unit;

a tube connecting the pump unit and the handpiece for transmitting irrigation liquid from the pump to the handpiece;

an electric switch detachably connected to the handpiece, the handpiece having a knob, the electric switch having a body defining an interior, the switch further comprising:

a first flexible conductor contained within the interior of the switch body;

a second flexible conductor contained within the interior of the switch body;

a separating insulating plunger slidably positioned between the first conductor and the second conductor and extending out of the interior of the body, the separating plunger having a projection to detachably connect to a lower surface of the handpiece knob, whereby the longitudinal movement of the handpiece knob longitudinally moves the separating plunger to selectively insulate the first conductor from the second conductor.

25. A pumping unit for irrigating a surgical site, the pumping unit comprising:

a pump head forming a fluid inlet orifice and a fluid outlet orifice, the pump head having a longitudinal axis;

a motor having a bottom wall and a shaft extending into the pump head;

an impeller connected to the shaft within the pump head;

a motor deck secured to the pump head;

a motor bracket connected to the motor deck, the bracket having a portion engageable with the bottom wall of the motor to secure the motor to the motor deck, the motor bracket and motor deck arranged to cooperatively secure the motor therebetween;

a battery;

a battery case to contain the battery, the battery case being detachably connected to the motor deck, the motor bracket being independent of the battery case whereby the assembly of the motor deck, motor bracket and motor may be detached, as a unit, from the battery case; and a fitting connected to the fluid outlet orifice, the fitting forming a fluid flow path that is substantially parallel to the longitudinal axis.

26. A pumping unit for irrigating a surgical site, the pumping unit comprising:

a pump head having a spike and a fluid outlet orifice, the spike forming a fluid inlet orifice;

a motor;

a housing receptive to the motor and to a battery for powering the motor; and a motor bracket connecting the motor to the pump head to enable the connected motor, bracket and pump head to be detachably connected, as a unit, from the housing.

27. A pumping unit for irrigating a surgical site, the pumping unit having a longitudinal axis and further comprising:

a pump head;

a fluid inlet orifice formed by the pump head;

a fluid outlet orifice formed by the pump head;

a fitting connected to the fluid outlet orifice and being external to the pump head, the fitting forming a fluid flow path that is substantially parallel to the longitudinal axis of the pump unit.

* * * * *